(12) United States Patent
Chambers et al.

(10) Patent No.: US 6,198,011 B1
(45) Date of Patent: Mar. 6, 2001

(54) SOLVENTS FOR USE IN FLUORINATION REACTIONS

(75) Inventors: Richard D. Chambers; Andrew R. Edwards, both of Durham (GB)

(73) Assignee: F2 Chemicals Ltd., Preston (GB)

( * ) Notice: Subject to any disclaimer, the term of this patent is extended or adjusted under 35 U.S.C. 154(b) by 0 days.

(21) Appl. No.: 09/230,973

(22) PCT Filed: Jun. 1, 1998

(86) PCT No.: PCT/GB98/01424

§ 371 Date: Mar. 25, 1999

§ 102(e) Date: Mar. 25, 1999

(87) PCT Pub. No.: WO98/55429

PCT Pub. Date: Dec. 10, 1998

(30) Foreign Application Priority Data

Jun. 5, 1997 (GB) .................................................. 9711588

(51) Int. Cl.$^7$ .................................................. C07C 17/20
(52) U.S. Cl. .................................................. 570/170
(58) Field of Search .................................................. 570/170

(56) References Cited

U.S. PATENT DOCUMENTS 4,978,769  12/1990  Kysela .

FOREIGN PATENT DOCUMENTS

| | | |
|---|---|---|
| 691197 * | 7/1964 | (CA) .................................... 570/170 |
| 0 190 393 | 8/1986 | (EP) . |
| P 499 930 | 8/1992 | (EP) . |
| 0 693 466 | 1/1996 | (EP) . |
| 2 664 589 | 1/1992 | (FR) . |
| WO 90/06296 | 6/1990 | (WO) . |

OTHER PUBLICATIONS

J. T. Maynard: The synthesis of highly fluorinated compounds by use of potassium fluoride in polar solvents: Journal of Organic Chemistry, vol. 28, No. 1, Jan. 1963, pp. 112–115, XP002077639 Easton US cited in the application see tables I–IV.

R. D. Chambers: perfluorocarbon fluids as solvent replacements: Journal of the Chemical Society, Perkin Transactions 1, No. 24, Dec. 21, 1997, pp. 3623–3627, XP002077640 Letchworth GB see the whole document.

* cited by examiner

Primary Examiner—Alan Siegel
(74) Attorney, Agent, or Firm—Nixon & Vanderhye

(57) ABSTRACT

A method of fluorinating an organic compound comprising reacting an organic compound with a fluorinating agent characterized in that a perfluorocarbon compound is present in the reaction medium. The perfluorocarbon compound may replace an amount of a solvent which would otherwise be required for the reaction to proceed efficiently. The perfluorocarbon compound is readily recoverable after reaction and may be re-used in subsequent reactions. Additives to the reaction medium, such as 18-crown-6, may increase the amoun of solvent which may be replaced. The method is beneficial where solvent consumption would otherwise be large, or where solvent recovery would otherwise be difficult.

6 Claims, 4 Drawing Sheets

1

Scheme 1

7

Scheme 2

SOLVENTS FOR USE IN FLUORINATION REACTIONS

FIELD OF THE INVENTION

The present invention relates to the fluorination of organic compounds.

BACKGROUND OF THE INVENTION

Considerable problems can arise with the use of conventional solvents in many types of chemical reactions including fluorination reactions. One problem often encountered is that of solvent recovery, which can often prove difficult and lead to solvent disposal problems. In addition, solvent consumption itself may be undesirably large and the solvent may present an explosion hazard. Thus, there exists a need to reduce the amount of solvent used in many reactions.

Surprisingly and beneficially, we have found that fluorination reactions carried out in the presence of a perfluorocarbon (PFC) fluid can require less solvent than would otherwise, i.e. conventionally, be used for the reaction to proceed efficiently.

Figure 1:
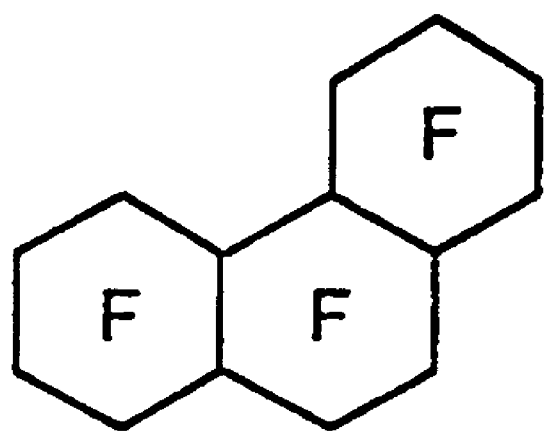

Perfluorocarbons are largely chemically inert, and are generally regarded as largely immiscible with most organic solvents, although published data is sparse. Miscibility with $CFCl_2CF_2Cl$ and some low molecular-weight hydrocarbons has been recorded, together with the fascinating solubility of gases such as oxygen, carbon dioxide and chlorine. Saturated perfluorocarbons (PFCs), e.g. perfluoroperhydrophenanthrene 1 shown in FIG. 1, are now industrially available over a wide boiling-point range.

STATEMENT OF THE INVENTION

According to the present invention, there is provided a method of fluorinating an organic compound, comprising reacting an organic compound with a fluorinating agent characterised in that a perfluorocarbon compound is present in the reaction medium.

The PFC may replace up to 100% of a solvent which would otherwise be required for the reaction to proceed efficiently.

Preferably, there is added to the reaction medium an amount of an additive which enables the amount of solvent to be reduced without substantial loss of fluorinating efficiency.

In addition to reducing the amount of solvent required, the use of PFCs according to the present method may also provide the following advantages.

The PFCs may be recovered simply by separation (possibly with cooling) and recycled without purification at the end of the reaction.

The use of PFC leads to reduced explosion hazards.

Figure 2:
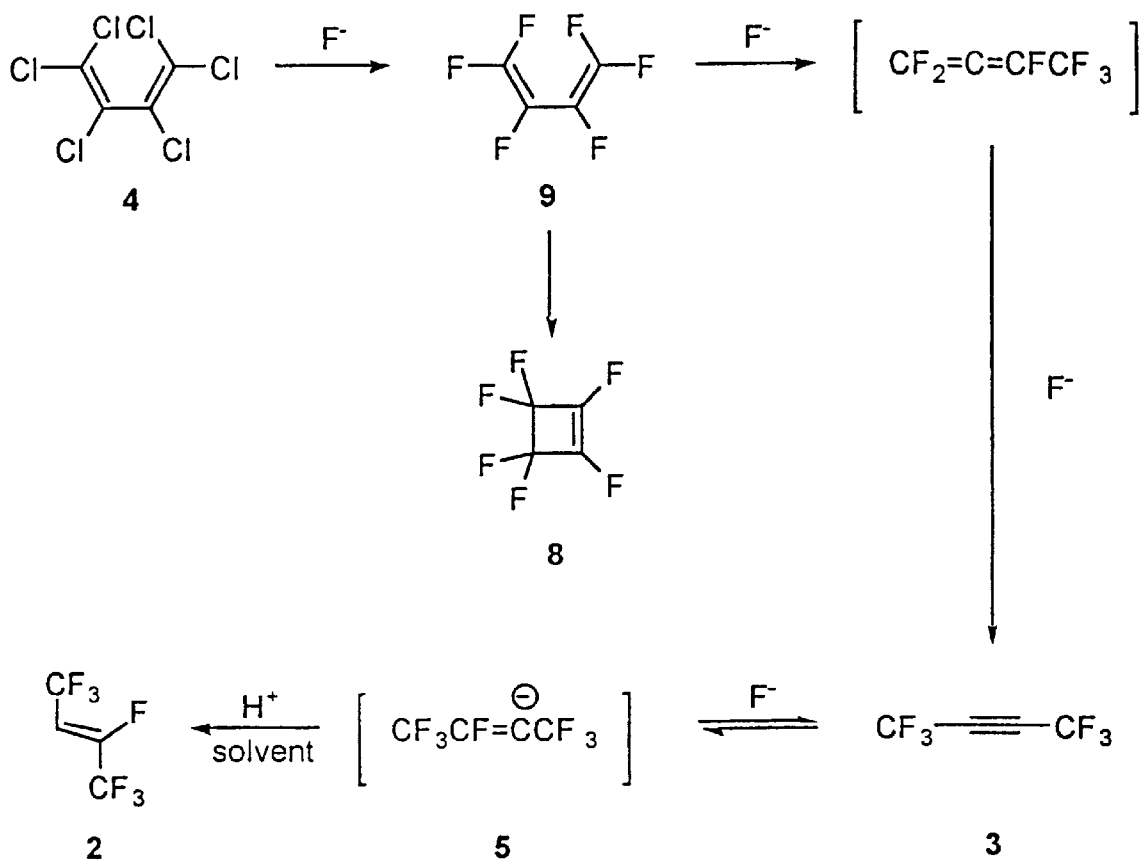

We have found that PFCs may be used effectively in the so-called 'Halex' process for exchange of chlorine by fluorine, using alkali-metal fluorides. This process is operated on the industrial scale for a number of products and solvent recovery can pose waste disposal problems. Furthermore, established procedures have proven hazardous (A. T. Cates, *J. Hazard. Mater.*, 1992, 1). The compounds 2H-heptafluorobut-2-ene 2 and hexafluorobut-2-yne 3, shown in FIG. 2, may be formed by the Halex process, a synthesis of 2 having been described by Maynard (J. T. Maynard, *J. Am. Chem. Soc.*, 1963, 28, 112). Overall, the reaction involves exchange of chlorine in hexachlorobutadiene 4 by fluorine, FIG. 2 Scheme 1, using potassium fluoride in an aprotic solvent. Typically, sulpholane, i.e. tetrahydrothiophene 1, 1-dioxide (THTD) may be used as the solvent, and it is curious that the proton in 2 most likely originates from the solvent in the final step of the process 3 to 2, via 5, although previously, the mechanism of formation of 2 had not been firmly established.

Surprisingly and beneficially, we have found that by using the method according to the present invention, a proportion of the THTD in the above Halex reaction may be replaced by a PFC. Preferably, perfluoroperhydrophenanthrene 1, bp 215° C., is used as the solvent replacement because of its high boiling point.

Typically, up to 90% v/v of the THTD solvent normally required (Maynard) may be replaced by an equivalent volume of 1.

Preferably, up to 75% v/v of the solvent normally required may be replaced by the equivalent volume of 1.

When replacing up to 75% of the normal THTD charge, reactions may be carried out efficiently using either a Carius tube, or atmospheric pressure conditions on a larger scale. Surprisingly, using the present method, the observed product contains ca. 75% of hexafluorobut-2-yne 3 and 25% of 2. We are unaware of any previous report of the direct synthesis of 3 from 4 and thus these observations, coupled with the recent finding that dehydrofluorination of 2 to the butyne 3 occurs on standing the former over molecular sieve (R. D. Chambers and A. J. Roche, *J. Fluorine Chem.*, 1996, 79, 121), provide a simple and novel laboratory synthesis of 3. We find that the 2H-heptafluorobut-2-ene 2, present in the product mixture, is converted quantitatively to 3 when the mixture of 3 and 2 is allowed to stand, in a sealed system, over 4 Å molecular sieve for 25 days. The alternative synthesis of 3 from 4 involves the use of antimony fluorides and/or hydrogen fluoride (A. L. Henne and W. G. Finnegan, *J. Am. Chem. Soc.*, 1949, 71, 298).

A reasonable explanation for the unique formation of 3 in the system containing the PFC 1, is that 3 is rapidly transferred to the perfluorocarbon layer and hence removed from access to the fluoride ion source, which otherwise promotes the conversion of 3 to 2, Scheme 1. This explanation is offered merely as a rationalisation of the results and does not limit the invention in any way.

The present method may be applied to the reaction of octachlorocyclopentene with potassium fluoride to form octafluorocyclopentene 6, shown in Table 1 below, and we find that, using the present method, only 25% of the normal THTD charge leads, in this case, to high conversions to 6 either using a Carius tube or atmospheric pressure conditions on a larger scale.

Similarly, we find that the present method can be equally applied to the synthesis of commercial products such as chlorofluoro-pyridines and -pyrimidines, and also to the synthesis of chlorofluorobenzene derivatives; these results are summarised in Table 1 below.

It is believed that the present method will be of benefit to workers who operate the above and like systems on a larger scale, and it is envisaged that the application of PFCs to systems with serious solvent recovery problems or systems with potentially serious heat-transfer problems will be particularly beneficial.

Preferably, an amount of an additive is added to the reaction medium which enables the solvent content to be reduced still further.

Using additives, essentially 'solventless' systems may be formed, wherein the PFC acts as a suspension medium. The additive may co-ordinate to the potassium, thereby making the fluoride available.

Figure 3:
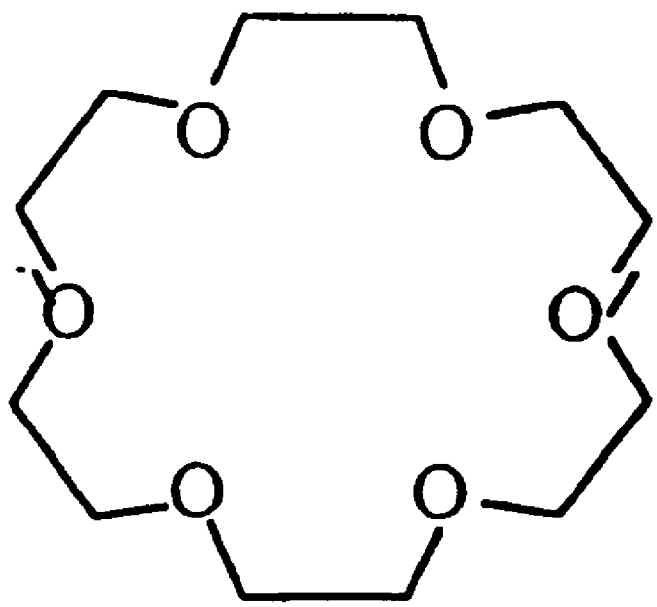

Suitable additives may include tetrabutylammonium bromide or 18-crown-6 7, shown in FIG. 3. 18-crown-6 7 is preferred. No fluorination is observed using either water or tetraglyme. Addition of 7 is found to be effective down to levels as low as 1% molar ratio, in relation to the chlorinated reactant, thus demonstrating the concept of potentially 'solventless' systems. However, the reactions proceed relatively slowly at these concentrations and therefore, to effect shorter reaction times, it is desirable to employ systems containing 10% molar equivalents of 7.

The PFC may be recovered essentially quantitatively by simple filtration from the residue. The polyether 7 may be mixed with the residual metal salts in the filtrate at this stage but can be easily removed by extraction with acetone. The recovered materials, without further purification but with addition of fresh potassium fluoride, may be used in a second cycle of reaction with octachlorocyclopentene. However, the second cycle of reaction is generally of reduced efficiency compared to the first and some further purification of the recovered 7 is desirable to maintain high efficiency in re-use. Examples of the application of PFCs containing additives to the synthesis of fluorinated aromatic compounds are shown in Table 2 below.

In the reactions with hexachlorobutadiene 4, the products from this reactant and the system containing 18-crown-6 7, remarkably, depends on the ratio of 7 used. When a molar ratio of 50% of 7 with 4 is used, the sole product is 2H-heptafluorobut-2-ene 2; a ratio 10% 7 gives hexafluorobut-2-yne 3 as the major product (72:10:18; 3:2:8), while a 1% ratio and using a sealed system gives hexafluorocyclobutene 8 as the product (68%), with small quantities of 3 and 2. The aforementioned observations indicate that the mechanism outlined in Scheme 1 operates, and that the availability of fluoride ion in the system is directly related to the concentration of polyether 7 used. Initial vinylic displacement of chloride by fluoride is believed to occur giving hexafluorobutadiene 9 which, at low concentrations of fluoride ion, will be preferentially extracted into the fluorocarbon phase and then, undergo the well established electrocyclisation to 8. This will also be favoured by the increased pressure associated with the use of a Carius tube. However, in the presence of higher ratios of fluoride, 9 is quickly converted to hexafluorobut-2-yne 3, again by established processes. This will then be extracted into the perfluorocarbon layer and consequently protected from further reaction. However, at high concentrations of fluoride, further reaction i.e. 3 to 5 to 2, competes.

Figure 4:
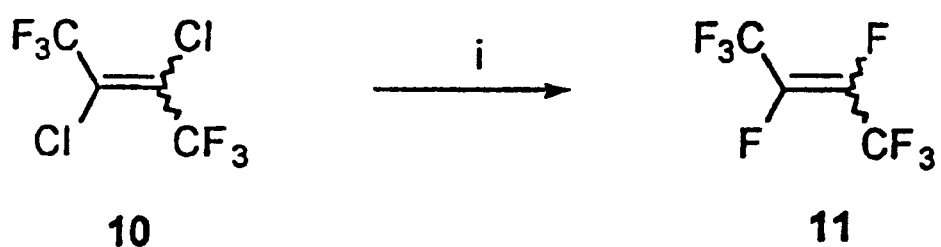

The conclusion that the process begins by vinylic displacement of chlorine by fluorine to give 9, rather than by attack accompanied by allylic displacement, is further confirmed by the fact that conversion of 10 to octafluorobut-2-ene 11, FIG. 4 scheme 2, is performed with very high efficiency and it is useful to note this perfluoroalkene was hitherto relatively inaccessible. In offering the foregoing explanation as a rationalisation of the results, it should be understood that this does not limit the invention in any way.

Whether the potassium fluoride is actually taken into solution in the perfluorocarbon layer by the 18-crown-6 7, or whether the latter remains solely in suspension is not definitely known. We have heated potassium permanganate and potassium picrate separately with 18-crown-6 7 and the perfluorocarbon 1 and in neither case did we have clear evidence of colour generated in the perfluorocarbon layer which would have indicated solubility and it seems unlikely that fluoride salts would be more soluble. On this basis, therefore, it appears that the 18-crown-6/potassium fluoride complex is essentially in suspension in the perfluorinated medium, as was described above for THTD, but that the proportions of 7 required for activating the metal fluoride are substantially less than for THTD.

Although the invention has been illustrated by way of reference to both the 'Halex' reaction and the use of perfluoroperhydrophenanthrene 1, it should be understood that this does not limit the invention in any way. The invention may be applied to many reactions other than Halex reactions having solvent problems. In principle, any perfluorocarbon fluid may be used in the method provided that the boiling point of the perfluorocarbon is above the temperature of the reaction involved. Perfluoroperhydrophenanthrene 1 is one perfluorocarbon suitable for use in the 'Halex' reaction because of its high boiling point (b.p 215° C.) compared to the high temperature of the reaction (200° C. approx.). Perfluorocarbons other than perfluoroperhydrophenanthrene may be used in the Halex reaction provided the boiling point is above the reaction temperature. For other types of fluorination reactions which are carried out at lower reaction temperatures any other perfluorocarbon fluids may be used provided that the boiling point of the perfluorocarbon is above the reaction temperature. Examples of perfluorocarbons include perfluoroperhydrophenanthrene, perfluoroperhydrofluoranthrene, perfluoroperhydrofluorene and perfluorodecalin.

The solvent replacement method of the present invention may also be applied to reactions other than fluorinations, e.g. oxidation using heavy metal salts.

Embodiments of the invention will now be described in detail by way of the following Examples only.

General Procedure for All Examples

All starting materials were obtained commercially and used as received. Sulfolane (tetrahydrothiophene 1,1-dioxide, THTD) was dried, prior to use, by distillation onto 4 Å molecular sieve and perfluoroperhydrophenanthrene PFC 1 (Flutec PP11, bp 215° C., as supplied by BNFL Fluorochemicals) was dried over 4 Å molecular sieve. $^{19}F$ and $^{1}H$ NMR spectra were recorded using either a Bruker AC 250, a Varian VXR 400S, or a Bruker AMX 500 NMR spectrometer. $^{13}C$ NMR spectra were recorded using either a Varian VXR 400S or a Bruker AMX 500 spectrometer. (Unless stated all samples run in $CDCl_3$, $^{19}F$ referenced to $CFCl_3$ and all J values are given in Hz). Infrared spectra were recorded on a Perkin-Elmer 1600 FT/IR spectrometer using KBr discs (solid samples) or thin films between two KBr plates (liquid samples), or a sealed gas cell fitted with KBr plates (gas samples). GLC mass spectra were obtained using a VG Trio 1000 spectrometer linked to a Hewlett-Packard 5890 Series II gas chromatograph fitted with a 25 m cross linked silicone capillary column. Carbon, hydrogen and nitrogen elemental analyses were obtained using a Carlo Erba 440 Elemental Analyser.

A. Reactions Using THTD

General Procedure for Examples 1 to 5 (Reactions in Carius Tubes)

A Carius tube (60 cm³), charged with potassium fluoride, PFC 1, THTD and chlorocarbon, was evacuated, sealed and heated in a rotating oil bath maintained at 190° C. After the reaction was completed the tube was opened and any volatile material transferred to a cold trap under reduced pressure. Further distillation under reduced pressure was carried out to afford a single product.

EXAMPLE 1

2H-Heptafluorobut-2-ene 2.—Hexachlorobuta-1,3-diene 4 (2.1 g, 8.1 mmol), potassium fluoride (4.7 g, 81 mmol), PFC 1 (6.5 cm$^3$) and THTD (2 cm$^3$), heated for 15 h gave 2H-heptafluorobut-2-ene (1.1 g, 60%); bp 8–10° C. (lit.,[8] 7–8° C.); $\upsilon_{max}$/cm$^{-1}$ 1050–1400 (CF), 1733 (C=C) and 3100 (CH); $\delta_F$ (235 MHz) –62.5 (3F, d, $^3J_{H-F}$ 28.4, 1-F), –77.0 (3F, s, 4-F), –119.7 (1F, s, 3-F); $\delta_C$ (100 MHz) 102.7 (qm, $^2J_{C-F}$ 38.9, 2-C), 117.5 (qd, $^1J_{C-F}$ 272.4, $^2J_{C-F}$ 38.9, 4-C), 120.8 (q, $^1J_{C-F}$ 269.5, 1-CF$_3$), 152.2 (dqq, $^1J_{C-F}$ 282.4, $^2J_{C-F}$ 39.7, $^3J_{C-F}$ 5.4, 3-C); $\delta_H$ (250 MHz) 5.57 (dq, $^3J_{H-F}$ 28.4, $^3J_{H-F}$ 6.9, 2-H); m/z (EI$^+$) 182 (M$^+$, 17.2%).

EXAMPLE 2

Octafluorocyclopentene 6.—Octachlorocyclopentene (3.4 g, 10 mmol), potassium fluoride (5.8 g, 100 mmol), PFC 1 (6.5 cm$^3$) and THTD (2 cm$^3$), heated for 15 h gave octafluorocyclopentene 6 (1.9 g, 89%); bp 26–28° C. (lit.,[15] 25.4–26.5° C.); $\upsilon_{max}$/cm$^{-1}$ 1769 and 1396 (C=C) and 986–1219 (CF); $\delta_F$ (376 MHz) –117.3 (2F, m, 3 and 5-F), –129.4 (1F, m, 4-F), –148.7 (1F, m, 1 and 2-F); $\delta_C$ (100 MHz) 109.1 (tpt, $^1J_{C-F}$ 278.0, $^2J_{C-F}$ 23.9, $^3J_{C-F}$ 4.9, 4-C), 110.3 (tqm, $^1J_{C-F}$ 260.1, $^2J_{C-F}$ 23.7, 3 and 5-C), 138.6 (dm, $^1J_{C-F}$ 297.9, 1 and 2-C); m/z (EI$^+$) 212 (M$^+$, 13.4%).

EXAMPLE 3

1,3,5-Trichloro-2,4,6-trifluorobenzene.— Hexachlorobenzene (1.0 g, 3.5 mmol), potassium fluoride (1.8 g, 31.6 mmol), PFC 1 (10 cm$^3$) and THTD (4.5 cm$^3$), heated for 200 h gave 1,3,5-trichloro-2,4,6-trifluorobenzene (0.7 g, 83%); mp 59–61° C. (lit.,[8] 57–61° C.); (Found: C, 30.3. C$_6$Cl$_3$F$_3$ requires C, 30.6%); $\upsilon_{max}$/cm$^{-1}$ 1603 (C=C) and 1445 (CF); $\delta_F$ (376 MHz, d$_6$-acetone) –114.8 (m); $\delta_C$ (100 MHz, d$_6$-acetone) 108.7 (td, $^2J_{C-F}$ 22.3, $^4J_{C-F}$ 4.9, 1-C), 154.7 (dt, $^1J_{C-F}$ 249.8, $^3J_{C-F}$ 4.5, 2-C); m/z (EI$^+$) 234 (M$^+$, 100%), 236 (M$^+$, 98.7%), 238 (M$^+$, 28.5%).

EXAMPLE 4

3,5-Dichlorotrifluoropyridine.—Pentachloropyridine (2.5 g, 10 mmol), potassium fluoride (4.0 g, 70 mmol), PFC 1 (6.5 cm$^3$) and THTD (2 cm$^3$), heated for 15 h gave 3,5-dichlorotrifluoropyridine (1.1 g, 60%); bp 157–159 ° C. (lit.,[16] 159–160° C.) (Found: C, 29.6; N, 6.9. C$_5$Cl$_2$F$_3$N requires C, 29.7; N, 6.9%); $\upsilon_{max}$/cm$^{-1}$ 1358–1434 (CF) and 1569–1604 (CN); $\delta_F$ (376 MHz) –70.0 (2F, d, $^4J_{F-F}$ 13.9, 2 and 6-F), –93.8 (1F, t, $^4J_{F-F}$ 14.3, 4-F); $\delta_C$ (100 MHz) 104.4 (m, 3 and 5-C), 155.8 (ddd, $^1J_{C-F}$ 246.0, $^4J_{C-F}$ 17.2, $^4J_{C-F}$ 10.8, 2 and 6-C), 164.8 (dt, $^1J_{C-F}$ 265.5, $^4J_{C-F}$ 5.3, 4-C); m/z (EI$^+$) 201 (M$^+$, 100%), 203 (M$^+$, 55.2%), 205 (M$^+$, 7.8%).

EXAMPLE 5

5-Chloroperfluoropyrimidine.—Tetrachloropyrimidine (2.2 g, 10 mmol), potassium fluoride (3.5 g, 60 mmol), PFC 1 (6.5 cm$^3$) and THTD (2 cm$^3$), heated for 15 h gave 5-Chloroperfluoropyrimidine (1.1 g, 60%); bp 115–116° C. (lit.,[17] 115° C.); (Found: C, 28.5; N, 16.5. C$_4$Cl$_1$F$_3$N$_2$ requires C, 28.5; N, 16.6%); $\upsilon_{max}$/cm$^{-1}$ 1417 (CF) and 1598–1640 (CN); $\delta_F$ (235 MHz) –43.1 (1F, s, 2-F), –55.8 (2F, s, 4 and 6-F); $\delta_C$ (100 MHz) 99.5 (td, $^2J_{C-F}$ 30.9, $^4J_{C-F}$ 10.0, 5-C), 158.0 (dt, $^1J_{C-F}$ 230.0, $^3J_{C-F}$ 21.6, 2-C), 168.6 (ddd, $^1J_{C-F}$ 261.0, $^3J_{C-F}$ 16.4, $^3J_{C-F}$ 10.3, 4 and 6-C); m/z (EI$^+$) 168 (M$^{30}$, 100%), 170 (M$^+$, 58.3%).

General Procedure for Examples 6 to 8 (Reactions at Atmospheric Pressure).

A round bottomed flask (500 cm$^3$) fitted with a reflux condenser, charged with potassium fluoride, PFC 1 (70 cm$^3$), THTD (30 cm$^3$) and chlorocarbon was heated to 190° C. and the contents stirred mechanically. After the reaction was complete, the flask. was allowed to cool and any volatile material transferred to a cold trap under reduced pressure. Further distillation under reduced pressure afforded a single product.

EXAMPLE 6

Octafluorocyclopentene 6.—Octachlorocyclopentene (17.2 g, 50 mmol) and potassium fluoride (34.8 g, 600 mmol) heated for 2 d gave octafluorocyclopentene 2 (6.1 g, 58%); see above for spectroscopic data.

EXAMPLE 7

3,5-Dichlorotrifluoropyridine.—Pentachloropyridine (6.3 g, 25 mmol) and potassium fluoride (11.6 g, 200 mmol) was heated for 3 d. After this time the flask was allowed to cool and the contents filtered, leaving a bi-phasic mixture; the lower layer (PFC 1) was colourless and the upper (THTD) was orange. The layers were separated and worked up independently. The PFC layer was extracted with toluene (3×70 cm$^3$) and the solvent removed by rotatory evaporation yielding a colourless oil which solidified. The THTD layer was distilled under reduced pressure and yielded an identical sample of this colourless material. The two samples were combined and gave 3,5-dichlorotrifluoropyridine (4.7 g, 93%); see above for spectroscopic data.

EXAMPLE 8

Hexafluorobut-2-yne 3.—Hexachlorobuta-1,3-diene 4 (261 g, 1 mol) was added dropwise over 2 h to a mechanically stirred suspension of freshly dried potassium fluoride (500 g, 8.5 mol) in anhydrous THTD (0.3l) and PFC 1 (1l), maintained at 190° C. The reaction was stirred for a further 4 h after the final addition of the diene, whilst volatile products (96 g) were collected in two sequential traps maintained at liquid air temperatures and were identified by comparison to authentic spectra as hexafluorobut-2-yne 3 (43% by $^{19}$F NMR integration) and 2H-heptafluorobut-2-ene 2 (14.3%). The volatiles were condensed over 4 Å molecular sieve[6] under reduced pressure and allowed to stand at room temperature for 25 d. After this time further analysis of a representative sample showed that the volatiles contained only hexafluorobut-2-yne[10] 3 (91 g, 56% based on starting diene 4); $\upsilon_{max}$/cm$^{-1}$ 1188 and 1279 (CF) and 2360 (C≡C); $\delta_F$ (235 MHz) –55.6 (s); $\delta_C$ (100 MHz) 30.0 (q, $^2J_{C-F}$ 19.4, 2 and 3-C), 113.9 (q, $^1J_{C-F}$ 259.8, 1 and 4-C).

B. Reactions Using 18-Crown-6

General Procedure for Examples 9 to 15 (Reactions in Carius Tubes)

A Carius tube (60 cm$^3$), charged with potassium fluoride, PFC 1 (20 cm$^3$), 18-crown-6 7 and chlorocarbon, was evacuated, sealed and heated in a rotating oil bath maintained at 190° C. After the reaction was complete, the tube-was opened and any volatile material transferred to a cold trap under reduced pressure. Additional distillation under reducedpressure was carried out to effect further purification.

EXAMPLE 9

Hexafluorocyclobutene 8.—Hexachlorobuta-1,3-diene 4 (2.6 g, 10 mmol), potassium fluoride (5.8 g, 100 mmol) and 18-crown-6 7 (0.3 g, 1 mmol), heated for 15 h gave hexafluorocyclobutene 8 (1.1 g, 68%); bp 0–2° C. (lit.,[18] 1.1° C.); $\upsilon_{max}$/cm$^{-1}$ 1794 and 1416 (C=C) and 980–1385 (CF); $\delta_F$ (471 MHz)–122.2 (2F, m, 3 and 4-F), –131.4 (1F, m, 1 and 2-F); $\delta_C$ (126 MHz) 114.1 (tm, $^1J_{C-F}$ 285.0, 3 and 4-C), 135.1 (dm, $^1J_{C-F}$ 337.5, 1 and 2-C); m/z (EI$^+$) 162 (M$^+$, 3.4%).

EXAMPLE 10

2H-Heptafluorobut-2-ene 2.—Hexachlorobuta-1,3-diene 4 (2.6 g, 10 mmol), potassium fluoride (4.6 g, 80 mmol) and 18-crown-6 7 (1.3 g, 5 mmol), heated for 15 h gave 2H-heptafluorobut-2-ene 2.(1.0 g, 55%); see above for spectroscopic data.

EXAMPLE 11

Octafluorobut-2-ene 11.—2,3-Dichlorohexafluorobut-2-ene 10 (2.3 g, 10 mmol), potassium fluoride (2.3 g, 40 mmol) and 18-crown-6 7 (0.3 g, 1 mmol), heated for 48 h gave E/Z octafluorobut-2-ene (3:1 ratio) 11 (1.8 g, 90.0%); bp 0–5° C. (lit., [14] 0.9° C.); $\upsilon_{max}$/cm$^{-1}$ (mixture of isomers) 1598 and 1727 (C=C) and 1115–1350 (CF); $\delta_F$ (471 MHz) E-isomer −71.9 (3F, m, 1-F), −162.7 (1F, m, 2-F), Z-isomer −69.3 (3F, m, 1-F), −145.9 (1F, m, 2-F); $\delta_C$(126 MHz)E-isomer 117.7 (qdm, $^1J_{C\text{-}F}$ 273.1, $^2J_{C\text{-}F}$ 30.1, 1-C), 142.1 (m, 2-C), Z-isomer 117.2 (qdm, $^1J_{C\text{-}F}$ 272.2, $^2J_{C\text{-}F}$ 38.9, 1-C), 140–144 (brm, 2-C); m/z (EI$^+$) 200 (M$^+$, 10.1%).

EXAMPLE 12

1,3,5-Trichloro-2,4,6-trifluorobenzene.—Hexachlorobenzene (2.9 g, 10 mmol), potassium fluoride (4.6 g, 80 mmol) and 18-crown-6 7 (0.3 g, 1 mmol), heated for 216 h gave 1,3,5-trichloro-2,4,6-trifluorobenzene (60% by GCMS integration) and, presumably, 1,2,3,5,-tetrachloro-4,6-difluorobenzene (40%); m/z (EI$^+$) 252 (M$^+$, 100%).

EXAMPLE 13

3,5-Dichlorotrifluoropyridine.—Pentachloropyridine (2.5 g, 10 mmol), potassium fluoride (4.0 g, 70 mmol) and 18-crown-6 7 (0.3 g, 1 mmol), heated for 15 h gave 3,5-dichlorotrifluoropyridine (1.7 g, 84%); see above for spectroscopic data.

EXAMPLE 14

5-Chloroperfluoropyrimidine.—Tetrachloropyrimidine (3.3 g, 15 mmol), potassium fluoride (4.6 g, 80 mmol) and 18-crown-6 7 (0.4 g, 1.5 mmol), heated for 15 h gave 5-chloroperfluoropyrimidine.(2.3 g, 91%); see above for spectroscopic data.

EXAMPLE 15

Octafluorocyclopentene 6.—Octachlorocyclopentene (1.7 g, 5 mmol), potassium fluoride (3.5 g, 60 mmol) and 18-crown-6 7 (0.1 g, 0.5 mmol), heated for 15 h gave octafluorocyclopentene 6 (1.1 g, 100%). The PFC slurry was then filtered and 18-crown-6 extracted from the inorganic residues using acetone (3×10 cm$^3$). The acetone was removed on a rotatory evaporator and the 18-crown-6 used in a repeat reaction without further purification along with the recovered PFC, as follows. Octachlorocyclopentene (1.5 g, 4.4 mmol), potassium fluoride (3.5 g, 60 mmol) and the recovered material, heated for 15 h gave octafluorocyclopentene 6 (0.7 g, 75%); see above for spectroscopic data.

General Procedure for Examples 16 to 17 (Reactions in Stirred Autoclaves).

A stirred autoclave (500 ml), charged with potassium fluoride, PFC 1 (50 ml), 18-crown-6 7 and chlorocarbon, was evacuated, sealed and heated in a furnace maintained at 190° C., whilst being stirred continuously. After the reaction was complete the autoclave was cooled, opened and any volatile material transferred to a cold trap under reduced pressure. Additional distillation under reduced pressure was carried out to effect further purification.

EXAMPLE 16

Octafluorocyclopentene 6.—Octachlorocyclopentene (5.0 g, 14.4 mmol), potassium fluoride (10.0 g, 172.4 mmol) and 18-crown-6 7 (0.4 g, 1.4 mmol), heated for 120 h gave octafluorocyclopentene 6 (2.3 g, 74%); see above for spectroscopic data.

EXAMPLE 17

3,5-Dichlorotrifluoropyridine.—Pentachloropyridine (5.0 g, 20.0 mmol), potassium fluoride (10.0 g, 172.4 mmol) and 18-crown-6 7 (0.5 g, 2.0 mmol), heated for 40 h gave 3,5-dichlorotrifluoropyridine (2.8 g, 69%) after filtration and extraction of the PFC layer with toluene (3×70 cm$^3$), removal of solvent and subsequent distillation; see above for spectroscopic data.

General Procedure for Examples 18 to 20 (Reactions at Atmospheric Pressure).

A round bottomed flask (250 cm$^3$) fitted with a reflux condenser, charged with potassium fluoride, PFC 1, 18-crown-6 7 and chlorocarbon was heated to 190° C. and the contents stirred mechanically for 4 d. After this time the flask was allowed to cool and any volatile material transferred to a cold trap under reduced pressure. Additional distillation under reduced pressure was carried out to effect further purification.

EXAMPLE 18

3,5-Dichlorotrifluoropyridine.—Pentachloropyridine (5.0 g, 20 mmol), potassium fluoride (9.2 g, 159.2 mmol), PFC 1 (50 cm$^3$) and 18-crown-6 7 (0.5 g, 2 mmol) gave 3,5-dichlorotrifluoropyridine (2.6 g, 65%) after filtration and extraction of the PFC layer with toluene (3×70 cm$^3$), removal of solvent and subsequent distillation; see above for spectroscopic data.

EXAMPLE 19

5-Chloroperfluoropyrimidine.—Tetrachloropyrimidine (3.3 g, 15 mmol), potassium fluoride (5.0 g, 86.2 mmol), PFC 1 (20 cm$^3$) and 18-crown-6 7 (0.7 g, 2.8 mmol) gave 5-Chloroperfluoropyrimidine (1.6 g, 69%); see above for spectroscopic data.

EXAMPLE 20

Hexafluorobut-2-yne 3.—Hexachlorobuta-1,3-diene 4 (240.0 g, 0.9 mol) was added dropwise over 2 h to a mechanically stirred suspension of freshly dried potassium fluoride (580.0 g, 10.0 mol), 18-crown-6 7 (26.4 g, 0.1 mol) and PFC 1 (1.5 l), maintained at 190° C. The reaction was stirred for a further 4 h after the final addition of the diene. Volatile products (83 g) were collected in two sequential traps maintained at liquid air temperatures and products were identified by comparison to authentic spectra as hexafluorobut-2-yne[19] 3 (72% by $^{19}$F NMR integration), 2H-heptafluorobut-2-ene[8] 2 (10%) and hexafluorocyclobutene[18] 8 (18%); see above for spectroscopic data.

TABLE 1

Fluorination of chlorocarbons using KF and 25% v/v of THTD

| Chlorocarbon | % THTD[a] | CT[b]/AP[c] | Products | Yield (%) |
|---|---|---|---|---|
| 4 | 25 | AP | 3 | 56[d] |
|  | 10 | AP | No reaction | — |
|  | KF coated[e] | AP | No reaction | — |
|  | 25 | CT | 2 | 60 |
| (cyclopentenyl-Cl) | 25 | AP | (cyclopentenyl-F) | 58 |
|  | 25 | CT | 6 | 89 |
|  | 0 | CT | No reaction | — |
| (3-chloropyridine) | 25 | AP | (3,5-dichloro-4-fluoropyridine) | 93 |
|  | 25 | CT | " | 59 |
|  | 0 | CT | No reaction | — |
| (2-chloropyrimidine) | 25 | CT | (2-chloro-5-fluoropyrimidine) | 71 |
| (chlorobenzene) | 25 | CT | (2,4,6-trichloro-3-fluoropyridine-like) | 83 |

[a]Volume %
[b]Carius Tube
[c]Atmospheric Pressure
[d]% After leaving over molecular sieve for 25 days[6]
[e]The potassium fluoride used had been soaked in THTD and the excess solvent decanted off.

TABLE 2

Fluorination of aromatics using KF, perfluorocarbon and 18-crown-67

| Chlorocarbon | Products | Yield (%) |
|---|---|---|
| (3-chloropyridine) | (3,5-dichloro-4-fluoropyridine) | 84 |
| (2-chloropyrimidine) | (2-chloro-5-fluoropyrimidine) | 91 |
| (chlorobenzene) | (2,6-dichloro-4-chloro-3-fluoropyridine) | 60 |

What is claimed is:

1. A method of fluorinating a chlorine containing organic compound comprising reacting in a solvent reaction medium the organic compound with an alkali metal fluoride wherein the solvent at least before the reaction starts comprises a perfluorocarbon.

2. The method according to claim 1 wherein the perfluorocarbon compound forms up to 100% of the solvent.

3. The method according to claim 2 wherein the solvent also comprises tetrahydrothiophene-1,1-dioxide.

4. The method according to claim 2 wherein an additive capable of coordinating to the alkali metal of the alkali metal fluoride is added to the reaction medium.

5. The method according to claim 4 wherein the additive is 18-crown-6.

6. The method according to claim 1 wherein the perfluorocarbon is perfluoroperhydrophenanthrene.

* * * * *

UNITED STATES PATENT AND TRADEMARK OFFICE
CERTIFICATE OF CORRECTION

PATENT NO. : 6,198,011 B1  
DATED : March 6, 2001  
INVENTOR(S) : Chambers et al Page 1 of 1

It is certified that error appears in the above-identified patent and that said Letters Patent is hereby corrected as shown below:

<u>Columns 9 and 10</u>  
Tables 1 and 2 delete "

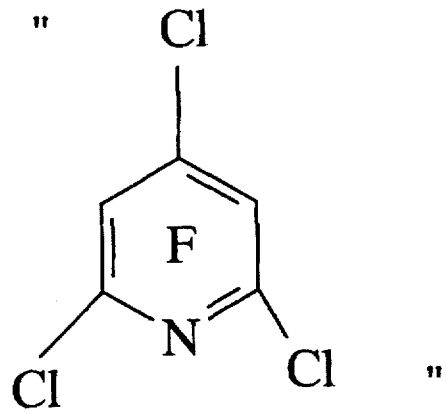

"

and insert the following --

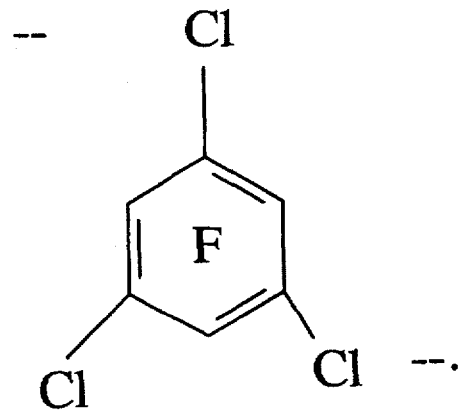

--.

Signed and Sealed this

Fourth Day of September, 2001

Attest:

*Nicholas P. Godici*

NICHOLAS P. GODICI  
*Attesting Officer*  *Acting Director of the United States Patent and Trademark Office*